United States Patent
Quincy, III et al.

(10) Patent No.: US 7,582,308 B2
(45) Date of Patent: *Sep. 1, 2009

(54) ODOR CONTROL COMPOSITION

(75) Inventors: Roger B. Quincy, III, Cumming, GA (US); John G. MacDonald, Decatur, GA (US)

(73) Assignee: Kimberly-Clark worldwide, Inc., Neenah, WI (US)

( * ) Notice: Subject to any disclaimer, the term of this patent is extended or adjusted under 35 U.S.C. 154(b) by 1156 days.

This patent is subject to a terminal disclaimer.

(21) Appl. No.: 10/328,730

(22) Filed: Dec. 23, 2002

(65) Prior Publication Data

US 2004/0120921 A1 Jun. 24, 2004

(51) Int. Cl.
*A01N 25/34* (2006.01)
*A61F 13/00* (2006.01)
*A61K 9/70* (2006.01)
*A01N 59/16* (2006.01)
*A61K 33/24* (2006.01)

(52) U.S. Cl. .................. 424/402; 424/443; 424/617

(58) Field of Classification Search .............. 424/402, 424/443, 617
See application file for complete search history.

(56) References Cited

U.S. PATENT DOCUMENTS

| | | |
|---|---|---|
| 2,015,864 A | 10/1935 | Müller et al. |
| 2,593,146 A | 4/1952 | Howard |
| 3,266,973 A | 8/1966 | Crowley |
| 3,338,992 A | 8/1967 | Kinney |
| 3,341,394 A | 9/1967 | Kinney |
| 3,381,688 A | 5/1968 | Satas |
| 3,494,821 A | 2/1970 | Evans |
| 3,502,538 A | 3/1970 | Petersen |
| 3,502,763 A | 3/1970 | Hartmann |
| 3,507,269 A | 4/1970 | Berry |
| 3,542,615 A | 11/1970 | Dobo et al. |
| 3,615,478 A | 10/1971 | Hoshino et al. |
| 3,692,618 A | 9/1972 | Dorschner et al. |
| 3,794,497 A | 2/1974 | Pratt et al. |
| 3,802,817 A | 4/1974 | Matsuki et al. |
| 3,849,241 A | 11/1974 | Butin et al. |
| 3,919,437 A | 11/1975 | Brown et al. |
| 3,960,494 A | 6/1976 | Verma et al. |
| 3,971,665 A | 7/1976 | Suzuki et al. |
| 4,006,030 A | 2/1977 | Yoshida et al. |
| 4,041,203 A | 8/1977 | Brock et al. |
| 4,078,029 A | 3/1978 | Yoshida et al. |
| 4,100,324 A | 7/1978 | Anderson et al. |
| 4,101,638 A | 7/1978 | Inoue et al. |
| 4,144,370 A | 3/1979 | Boulton |
| 4,172,781 A | 10/1979 | Walk et al. |
| 4,297,233 A | 10/1981 | Gualandi |
| RE30,797 E | 11/1981 | Davis |
| RE30,803 E | 11/1981 | Davis |
| 4,313,820 A | 2/1982 | Farha, Jr. et al. |
| 4,340,563 A | 7/1982 | Appel et al. |
| 4,375,448 A | 3/1983 | Appel et al. |
| 4,407,960 A | 10/1983 | Tratnyek |
| 4,467,012 A | 8/1984 | Pedersen et al. |
| 4,469,746 A | 9/1984 | Weisman et al. |
| 4,488,969 A | 12/1984 | Hou |
| 4,494,278 A | 1/1985 | Kroyer et al. |
| 4,494,629 A | 1/1985 | Raeburn |
| 4,517,308 A | 5/1985 | Ehlenz et al. |
| 4,522,203 A | 6/1985 | Mays |
| 4,525,410 A | 6/1985 | Hagiwara et al. |
| 4,575,556 A | 3/1986 | Byrne et al. |
| 4,604,313 A | 8/1986 | McFarland et al. |
| 4,640,810 A | 2/1987 | Laursen et al. |
| 4,643,801 A | 2/1987 | Johnson |
| 4,655,757 A | 4/1987 | McFarland et al. |
| 4,701,218 A | 10/1987 | Barker et al. |
| 4,715,983 A | 12/1987 | Ota et al. |
| 4,725,415 A | 2/1988 | Kidd |
| 4,734,324 A | 3/1988 | Hill |
| RE32,649 E | 4/1988 | Brandt et al. |
| 4,775,585 A | 10/1988 | Hagiwara |
| 4,780,448 A | 10/1988 | Broecker et al. |
| 4,781,858 A | 11/1988 | Mizukami et al. |
| 4,783,220 A | 11/1988 | Gamble et al. |
| 4,798,603 A | 1/1989 | Meyer et al. |
| 4,802,473 A | 2/1989 | Hubbard et al. |

(Continued)

FOREIGN PATENT DOCUMENTS

EP 0103214 B1 3/1984

(Continued)

OTHER PUBLICATIONS

Article—*Saponins and Sapogenins. VIII. Surface Films of Echinocystic Acid and Derivatives*, C.R. Noller, J. Am. Chem. Soc., vol. 60, 1938, 3 pages.

(Continued)

*Primary Examiner*—Yong S Chong
(74) *Attorney, Agent, or Firm*—Dority & Manning, P.A.

(57) ABSTRACT

An odor control composition that includes a silicon oxide compound and a transition metal in an amount of from about 0.2 wt. % to about 10 wt. % of the odor control composition is provided. The silicon oxide compound is formed from a silicon source and a template (e.g., cyclodextrin template).

36 Claims, 1 Drawing Sheet

U.S. PATENT DOCUMENTS

| | | |
|---|---|---|
| 4,818,464 A | 4/1989 | Lau |
| 4,823,404 A | 4/1989 | Morell et al. |
| 4,823,803 A | 4/1989 | Nakamura |
| 4,904,304 A | 2/1990 | Watanabe et al. |
| 4,969,457 A | 11/1990 | Hubbard et al. |
| 4,978,615 A | 12/1990 | Aoyama et al. |
| 4,988,505 A | 1/1991 | Watanabe et al. |
| 5,000,746 A | 3/1991 | Meiss |
| 5,020,533 A | 6/1991 | Hubbard et al. |
| 5,057,302 A | 10/1991 | Johnson et al. |
| 5,064,473 A | 11/1991 | Kubo et al. |
| 5,100,581 A | 3/1992 | Watanabe et al. |
| 5,100,702 A | 3/1992 | Maeda et al. |
| 5,108,739 A | 4/1992 | Kurihara et al. |
| 5,122,418 A | 6/1992 | Nakane et al. |
| 5,133,803 A | 7/1992 | Moffatt |
| 5,145,518 A | 9/1992 | Winnik et al. |
| 5,145,727 A | 9/1992 | Potts et al. |
| 5,169,706 A | 12/1992 | Collier, IV et al. |
| 5,178,931 A | 1/1993 | Perkins et al. |
| 5,183,656 A | 2/1993 | Uesaka et al. |
| 5,188,885 A | 2/1993 | Timmons et al. |
| 5,196,177 A | 3/1993 | Watanabe et al. |
| 5,204,429 A | 4/1993 | Kaminsky et al. |
| 5,209,998 A | 5/1993 | Kavassalis et al. |
| 5,220,000 A | 6/1993 | Theodoropulos |
| 5,221,497 A | 6/1993 | Watanabe et al. |
| 5,225,374 A | 7/1993 | Fare et al. |
| 5,230,953 A | 7/1993 | Tsugeno et al. |
| 5,238,518 A | 8/1993 | Okubi et al. |
| 5,245,117 A | 9/1993 | Withers et al. |
| 5,266,289 A | 11/1993 | Tsugeno et al. |
| 5,284,703 A | 2/1994 | Everhart et al. |
| 5,292,868 A | 3/1994 | Subramanian |
| 5,294,717 A | 3/1994 | Theodoropulos |
| 5,300,365 A | 4/1994 | Ogale |
| 5,322,061 A | 6/1994 | Brunson |
| 5,332,432 A | 7/1994 | Okubi et al. |
| 5,338,713 A | 8/1994 | Takagi et al. |
| 5,342,876 A | 8/1994 | Abe et al. |
| 5,350,624 A | 9/1994 | Georger et al. |
| 5,366,947 A | 11/1994 | Müller et al. |
| 5,382,400 A | 1/1995 | Pike et al. |
| 5,383,450 A | 1/1995 | Hubbard et al. |
| 5,397,667 A | 3/1995 | Law et al. |
| 5,407,442 A | 4/1995 | Karapasha |
| 5,407,600 A | 4/1995 | Ando et al. |
| 5,420,090 A | 5/1995 | Spencer et al. |
| 5,427,844 A | 6/1995 | Murai et al. |
| 5,429,628 A | 7/1995 | Trinh et al. |
| 5,451,450 A | 9/1995 | Erderly et al. |
| 5,458,864 A | 10/1995 | Tsugeno et al. |
| 5,472,775 A | 12/1995 | Obijeski et al. |
| 5,480,636 A | 1/1996 | Maruo et al. |
| 5,486,356 A | 1/1996 | Yim |
| 5,487,938 A | 1/1996 | Spencer et al. |
| 5,488,126 A | 1/1996 | Subramanian et al. |
| 5,527,171 A | 6/1996 | Soerensen |
| 5,538,548 A | 7/1996 | Yamazaki |
| 5,539,124 A | 7/1996 | Etherton et al. |
| 5,540,916 A | 7/1996 | Parks |
| 5,547,607 A | 8/1996 | Ando et al. |
| 5,553,608 A | 9/1996 | Reese et al. |
| 5,554,775 A | 9/1996 | Krishnamurti et al. |
| 5,580,655 A | 12/1996 | El-Shall et al. |
| 5,583,219 A | 12/1996 | Subramanian et al. |
| 5,591,797 A | 1/1997 | Barthel et al. |
| 5,597,512 A | 1/1997 | Watanabe et al. |
| 5,661,198 A | 8/1997 | Inatani et al. |
| 5,663,224 A | 9/1997 | Emmons et al. |
| 5,679,138 A | 10/1997 | Bishop et al. |
| 5,679,724 A | 10/1997 | Sacripante et al. |
| 5,695,868 A | 12/1997 | McCormack |
| 5,733,272 A | 3/1998 | Brunner et al. |
| 5,747,003 A | 5/1998 | Mohnot et al. |
| 5,773,227 A | 6/1998 | Kuhn et al. |
| 5,795,985 A | 8/1998 | Hüsler et al. |
| 5,813,398 A | 9/1998 | Baird et al. |
| 5,817,300 A | 10/1998 | Cook et al. |
| 5,837,352 A | 11/1998 | English et al. |
| 5,843,509 A | 12/1998 | Calvo Salve et al. |
| 5,855,788 A | 1/1999 | Everhart et al. |
| 5,861,144 A | 1/1999 | Peterson et al. |
| 5,871,872 A | 2/1999 | Matijevic et al. |
| 5,874,067 A | 2/1999 | Lucas et al. |
| 5,880,176 A | 3/1999 | Kamoto et al. |
| 5,880,309 A | 3/1999 | Suzuki et al. |
| 5,882,638 A | 3/1999 | Dodd et al. |
| 5,885,599 A | 3/1999 | Peterson et al. |
| 5,897,541 A | 4/1999 | Uitenbroek et al. |
| 5,902,226 A | 5/1999 | Tasaki et al. |
| 5,905,101 A | 5/1999 | Fujiki et al. |
| 5,916,596 A | 6/1999 | Desai et al. |
| 5,944,933 A | 8/1999 | Heller et al. |
| 5,948,398 A | 9/1999 | Hanamoto et al. |
| 5,948,483 A | 9/1999 | Kim et al. |
| 5,962,566 A | 10/1999 | Grandfils et al. |
| 5,964,926 A | 10/1999 | Cohen |
| 5,972,389 A | 10/1999 | Shell et al. |
| 5,985,229 A | 11/1999 | Yamada et al. |
| 5,989,510 A | 11/1999 | Abe et al. |
| 5,989,515 A | 11/1999 | Watanabe et al. |
| 6,004,625 A | 12/1999 | Ohshima |
| 6,007,592 A | 12/1999 | Kasai et al. |
| 6,024,786 A | 2/2000 | Gore |
| 6,045,900 A | 4/2000 | Haffner et al. |
| 6,047,413 A | 4/2000 | Welchel et al. |
| 6,060,410 A | 5/2000 | Gillberg-LaForce et al. |
| 6,073,771 A | 6/2000 | Pressley et al. |
| 6,075,179 A | 6/2000 | McCormack et al. |
| 6,096,299 A | 8/2000 | Guarracino et al. |
| 6,111,163 A | 8/2000 | McCormack et al. |
| 6,172,173 B1 | 1/2001 | Spencer et al. |
| 6,177,608 B1 | 1/2001 | Weinstrauch |
| 6,190,814 B1 | 2/2001 | Law et al. |
| 6,193,844 B1 | 2/2001 | McLaughlin et al. |
| 6,225,524 B1 | 5/2001 | Guarracino et al. |
| 6,238,767 B1 | 5/2001 | McCormack et al. |
| 6,254,894 B1 | 7/2001 | Denkewicz, Jr. et al. |
| 6,264,615 B1 | 7/2001 | Diamond et al. |
| 6,277,346 B1 | 8/2001 | Murasawa et al. |
| 6,277,772 B1 | 8/2001 | Gancet et al. |
| 6,291,535 B1 | 9/2001 | Watanabe et al. |
| 6,294,222 B1 | 9/2001 | Cohen et al. |
| 6,299,867 B1 | 10/2001 | Aoyagi et al. |
| 6,309,736 B1 | 10/2001 | McCormack et al. |
| 6,315,864 B2 | 11/2001 | Anderson et al. |
| 6,334,988 B1 | 1/2002 | Gallis et al. |
| 6,344,218 B1 | 2/2002 | Dodd et al. |
| 6,344,272 B1 | 2/2002 | Oldenburg et al. |
| 6,358,537 B1 | 3/2002 | Hoshino et al. |
| 6,358,909 B1 | 3/2002 | Ochomogo et al. |
| 6,369,290 B1 | 4/2002 | Glaug et al. |
| 6,376,741 B1 | 4/2002 | Guarracino et al. |
| 6,387,495 B1 | 5/2002 | Reeves et al. |
| 6,398,827 B1 | 6/2002 | Ota et al. |
| 6,410,765 B1 | 6/2002 | Wellinghoff et al. |
| 6,425,530 B1 | 7/2002 | Coakley |
| 6,427,693 B1 | 8/2002 | Blackstock et al. |
| 6,428,814 B1 | 8/2002 | Bosch et al. |
| 6,433,243 B1 | 8/2002 | Woltman et al. |
| 6,440,187 B1 | 8/2002 | Kasai et al. |
| 6,460,989 B1 | 10/2002 | Yano et al. |
| 6,461,735 B1 | 10/2002 | Furuya et al. |

| | | | | | | |
|---|---|---|---|---|---|---|
| 6,467,897 | B1 | 10/2002 | Wu et al. | EP | 1162172 A1 | 12/2001 |
| 6,468,500 | B1 | 10/2002 | Sakaguchi et al. | EP | 1188854 A1 | 3/2002 |
| 6,475,601 | B1 | 11/2002 | Sakaki et al. | EP | 1214878 A1 | 6/2002 |
| 6,479,150 | B1 | 11/2002 | Liu et al. | EP | 1216675 A1 | 6/2002 |
| 6,491,790 | B1 | 12/2002 | Proverb et al. | EP | 1298071 A1 | 4/2003 |
| 6,498,000 | B2 | 12/2002 | Murasawa et al. | EP | 1315526 B1 | 6/2003 |
| 6,517,199 | B1 | 2/2003 | Tomioka et al. | EP | 1053788 B1 | 10/2003 |
| 6,531,704 | B2 | 3/2003 | Yadav et al. | JP | 62149322 | 7/1987 |
| 6,536,890 | B1 | 3/2003 | Kato et al. | JP | 3221142 | 9/1991 |
| 6,548,264 | B1 | 4/2003 | Tan et al. | JP | 1 0314577 | 12/1998 |
| 6,551,457 | B2 | 4/2003 | Westman et al. | JP | 2002 2187712 | 7/2002 |
| 6,562,441 | B1 | 5/2003 | Maeda et al. | WO | WO 8902698 A1 | 4/1989 |
| 6,575,383 | B2 | 6/2003 | Dobler et al. | WO | WO 9111977 A1 | 8/1991 |
| 6,578,521 | B2 | 6/2003 | Raymond et al. | WO | WO 9112029 A1 | 8/1991 |
| 6,589,562 | B1 | 7/2003 | Shefer et al. | WO | WO 9112030 A1 | 8/1991 |
| 6,607,711 | B2 | 8/2003 | Pedersen | WO | WO 9619346 A2 | 6/1996 |
| 6,623,848 | B2 | 9/2003 | Brehm et al. | WO | WO 9619346 A3 | 6/1996 |
| 6,638,918 | B2 | 10/2003 | Davison et al. | WO | WO 9725076 A1 | 7/1997 |
| 6,639,004 | B2 | 10/2003 | Falat et al. | WO | WO 9820915 A1 | 5/1998 |
| 6,645,569 | B2 | 11/2003 | Cramer et al. | WO | WO 9826808 A2 | 6/1998 |
| 6,693,071 | B2 | 2/2004 | Ghosh et al. | WO | WO 9826808 A3 | 6/1998 |
| 2001/0000889 | A1 | 5/2001 | Yadav et al. | WO | WO 9947252 A3 | 9/1999 |
| 2001/0023338 | A1 | 9/2001 | Guarracino et al. | WO | WO 0003797 A1 | 1/2000 |
| 2001/0031248 | A1 | 10/2001 | Hall-Puzio et al. | WO | WO 0029036 A2 | 3/2000 |
| 2001/0056246 | A1 | 12/2001 | Rodriguez-Fernandez | WO | WO 0029036 A3 | 3/2000 |
| 2002/0005145 | A1 | 1/2002 | Sherman | WO | WO 00137764 | 3/2000 |
| 2002/0066542 | A1 | 6/2002 | Jakob et al. | WO | WO 0059555 A1 | 10/2000 |
| 2002/0091071 | A1 | 7/2002 | Fischer et al. | WO | WO 0076558 A1 | 12/2000 |
| 2002/0106466 | A1 | 8/2002 | Hausmann et al. | WO | WO 0106054 A1 | 1/2001 |
| 2002/0110686 | A1 | 8/2002 | Dugan | WO | WO 03025067 A1 | 3/2002 |
| 2002/0128336 | A1 | 9/2002 | Kolb et al. | WO | WO 0226272 A1 | 4/2002 |
| 2002/0141898 | A1* | 10/2002 | Carlucci et al. ............... 422/5 | WO | WO 0249559 A2 | 6/2002 |
| 2002/0142937 | A1 | 10/2002 | Carter et al. | WO | WO 02055115 A1 | 7/2002 |
| 2002/0149656 | A1 | 10/2002 | Nohr et al. | WO | WO 02062881 A2 | 8/2002 |
| 2002/0150678 | A1 | 10/2002 | Cramer et al. | WO | WO 02064877 A2 | 8/2002 |
| 2002/0176982 | A1 | 11/2002 | Rohrbaugh et al. | WO | WO 02064877 A3 | 8/2002 |
| 2002/0177621 | A1 | 11/2002 | Hanada | WO | WO 02083297 A1 | 10/2002 |
| 2002/0182102 | A1 | 12/2002 | Fontenot et al. | WO | WO 02084017 A1 | 10/2002 |
| 2003/0013369 | A1 | 1/2003 | Soane et al. | WO | WO 02094329 A1 | 11/2002 |
| 2003/0021983 | A1 | 1/2003 | Nohr et al. | WO | WO 02095112 A1 | 11/2002 |
| 2003/0050211 | A1 | 3/2003 | Hage et al. | WO | WO 03000979 A2 | 1/2003 |
| 2003/0056648 | A1 | 3/2003 | Fornai et al. | WO | WO 03032959 A1 | 4/2003 |
| 2003/0070782 | A1 | 4/2003 | Proverb et al. | WO | WO 03088931 A2 | 10/2003 |
| 2003/0082237 | A1 | 5/2003 | Cha et al. | WO | WO 03092885 A1 | 11/2003 |
| 2003/0100842 | A1 | 5/2003 | Rosenberg et al. | WO | WO 2004 000986 A1 | 12/2003 |
| 2003/0147956 | A1 | 8/2003 | Shefer et al. | | | |
| 2003/0147966 | A1 | 8/2003 | Franzen et al. | | | |
| 2003/0181540 | A1 | 9/2003 | Quellet et al. | | | |
| 2003/0203009 | A1 | 10/2003 | MacDonald | | | |
| 2003/0235605 | A1 | 12/2003 | Lelah et al. | | | |
| 2004/0033269 | A1 | 2/2004 | Hei et al. | | | |
| 2004/0034157 | A1 | 2/2004 | Ghosh et al. | | | |
| 2004/0043688 | A1 | 3/2004 | Soerens et al. | | | |
| 2004/0122387 | A1 | 6/2004 | Long et al. | | | |

FOREIGN PATENT DOCUMENTS

| | | |
|---|---|---|
| EP | 0232141 A1 | 8/1987 |
| EP | 0251783 B1 | 1/1988 |
| EP | 0282287 B2 | 9/1988 |
| EP | 0339461 B1 | 11/1989 |
| EP | 0348978 A2 | 1/1990 |
| EP | 0376448 B1 | 7/1990 |
| EP | 0389015 A2 | 9/1990 |
| EP | 0389015 A3 | 9/1990 |
| EP | 0389023 A2 | 9/1990 |
| EP | 0389023 A3 | 9/1990 |
| EP | 0483500 A1 | 5/1992 |
| EP | 0510619 A1 | 10/1992 |
| EP | 0749295 B1 | 12/1996 |
| EP | 0972563 A1 | 1/2000 |
| EP | 1034800 A1 | 9/2000 |
| EP | 1157672 A1 | 11/2001 |

OTHER PUBLICATIONS

Article—*Synthesis of porous Silica with help from cyclodextrin aggregates*, Markus Antonietti, Max-Planck-Institut für Kolloid-und, Germany, 1 page.

Article—*Immobilization of $(n\text{-}Bu_4N)_4W_{10}O_{32}$ on Mesoporous MCM-41 and Amorphous Silicas for Photocatalytic Oxidation of Cycloalkanes with Molecular Oxygen*, Andrea Maldotti, Alessandra Molinari, Graziano Varani, Maurizio Lenarda, Loretta Storaro, Franca Bigi, Raimondo Maggi, Allesandro Mazzacani, and Giovanni Sartori, Journal of Catalysis, vol. 209, 2002, pp. 210-216.

Article—*Fe-MCM-41 for Selective Epoxidation of Styrene with Hydrogen Peroxide*, Qinghong Zhang, Ye Wang, Satoko Itsuki, Tetsuya Shishido, and Katsuomi Takehira, The Chemical Society of Japan, Chemistry Letters 2001, pp. 946-947.

Article—*Mesoporous Sieves with Unified Hybrid Inorganic/Organic Frameworks*, Brian J. Melde, Brian T. Holland, Christopher F. Blanford, and Andreas Stein, Chem. Mater., vol. 11, No. 11, 1999, pp. 3302-3308.

Article—*From Cyclodextrin Assemblies to Porous Materials by Silica Templating*, Sebastian Polarz, Bernd Smarsly, Lyudmila Bronstein, and Markus Antonietti, Angew. Chem. Int., vol. 40, No. 23, 2001, pp. 4417-4421.

Article—*Adsorption of Dyes on Nanosize Modified Silica Particles*, Guangwei Wu, Athanasia Koliadima, Yie-Shein Her, and Egon Matijevic, Journal of Colloid and Interface Sciences, vol. 195, 1997, pp. 222-228.

Article—*Adsorption of Proteins and Antibiotics on Porous Alumina Membranes*, Yi Hua Ma, Aseem Bansal, and William M. Clark, Fundamentals of Adsorption, vol. 80, 1992, pp. 389-396.
Abstract of Japanese Patent No. 5106199, Apr. 27, 1993.
Abstract of Japanese Patent No. 9143872, Jun. 3, 1997.
Article—*Applicability of a SPME method for the Rapid Determination of VOCs*, Alexandre Béné, Jean-Luc Luisier, and Antoine Fornage, Chimia, vol. 56, No. 6, 2002, pp. 289-291.
Article—*Characterisation of novel modified active carbons and marine algal biomass for the selective adsorption of lead*, D.J. Malik, V. Strelko, Jr., M. Streat, and A.M. Puziy, Water Research, vol. 36, 2002, pp. 1527-1538.
Article—*Significance of Ammonia in the Genesis of Gastric Epithelial Lesions Induced by Helicobacter pylori: An in vitro Study with Different Bacterial Strains and Urea Concentrations*, P. Sommi, V. Ricci, R. Fiocca, M. Romano, K.J. Ivey, E. Cova, E. Solcia, and U. Ventura, Digestion, vol. 57, 1996, pp. 299-304.
Article—*Ammonia vapour in the mouth as a diagnostic marker for Helicobacter pylori infection: preliminary "proof of principle" pharmacological investigations*, C. D. R. Dunn, M. Black, D. C. Cowell, C. Penault, N. M. Ratcliffe, R. Spence, and C. Teare, British Journal of Biomedical Science, vol. 58, 2001, pp. 66-76.
Article—*Purification and Characterization of Urease from Helicobacter pylori*, Bruce E. Dunn, Gail P. Campbell, Guillermo I. Perez-Perez, and Martin J. Blaser, The Journal of Biological Chemistry, vol. 265, No. 16, Jun. 5, 1990, pp. 9464-1990.
Article—*Validation of $^{13}C$-Urea Breath Test for the Diagnosis of Helicobacter Pylori Infection in the Singapore Population*, T. S. Chua, K. M. Fock, E. K. Teo, T. M. Ng, Singapore Medical Journal, vol. 43, No. 8, 2002, pp. 408-411.
Article—*Significance of ammonia produced by Helicobacter pylori*, Shigeji Ito, Yoshihiro Kohli, Takuji Kato, Yoshimichi Abe, and Takashi Ueda, European Journal of Gastroenterology & Hepatology, vol. 6, No. 2, 1994, pp. 167-174.
Article—*Spectrophotometric Assay of Thiols*, Peter C. Jocelyn, Methods in Enzymology, vol. 142, 1987, pp. 44-67.
Abstract of Japanese Patent No. 7256025, Oct. 9, 1995.
Article—*Immunization of mice with peptomers covalently couopled to aluminum oxide nanoparticles*, Andreas Frey, Nicholas Mantis, Pamela A. Kozlowski, Alison J. Quayle, Adriana Bajardi, Juana J. Perdomo, Frank A. Robey, and Marian R. Neutra, Vaccine, vol. 17, 1999, pp. 3007-3019.
PCT Search Report for PCT/US03/39737, Jun. 18, 2004.
PCT Search Report for PCT/US03/32846, Jun. 7, 2004.
Abstract of SU834073, May 30, 1981.
PCT Search Report and Written Opinion for PCT/US2004/011596, Aug. 30, 2004.
PCT Search Report and Written Opinion for PCT/US2004/016933, Nov. 2, 2004.
Abstract of Japanese Patent No. JP1262868, Oct. 19, 1989.
Abstract of Japanese Patent No. JP2157039, Jun. 15, 1990.
Abstract of Japanese Patent No. JP3195562, Aug. 27, 1991.
Abstract of Japanese Patent No. JP4335141, Nov. 24, 1992.
Abstract of Japanese Patent No. JP5261246, Oct. 12, 1993.
Abstract of Japanese Patent No. JP6285140, Oct. 11, 1994.
Abstract of Japanese Patent No. JP63072337, Apr. 2, 1988.
Abstract of Japanese Patent No. JP8152409, Jun. 11, 1996.
U.S. Appl. No. 10/723,761, filed Nov. 26, 2004, Quincy, III, et al., Odor Control In Personal Care Products.
U.S. Appl. No. 10/955,316, filed Sep. 30, 2004, MacDonald, et al., Odor-Reducing Quinone Compounds.
Abstract of Japanese Patent No. JP04255767, Sep. 10, 1992.
Abstract of Japanese Patent No. JP05098185, Apr. 20, 1993.
Paper—*Uniform Deposition of Ultrathin Polymer Films on the Surfaces of $Al_2O_3$ Nanoparticles by a Plasma Treatment*, Donglu Shi, S. X. Wang, Wim J. van Ooij, L. M. Wang, Jiangang Zhao, and Zhou Yu, University of Cincinnati and University of Michigan, Jun. 2000, pp. 1-5.
Article—*Development of novel dye-doped silica nanoparticles for biomarker application*, Swadeshmukul Santra, Kemin Wang, Rovelyn Tapec, and Weihong Tan, Journal of Biomedical Optics, vol. 6, No. 2, Apr. 2001, pp. 160-166.
Article—*Nanoparticles based on polyelectrolyte complexes: effect of structure and net charge on the sorption capability for solved organic molecules*, H.-M. Buchhammer, G. Petzold, and K. Lunkwitz, Colloid Polym. Sci., vol. 278, 2000, pp. 841-847.
Article—*Adsorption of Gases in Multimolecular Layers*, Stephen Brunauer, P.H. Emmett, and Edward Teller, The Journal of the American Chemical Society, vol. 60, Feb. 1938, pp. 309-319.
Article—*Study of the urea thermal decomposition (pyrolysis) reaction and importance to cyanuric acid production*, Peter M. Schaber, James Colson, Steven Higgins, Ed Dietz, Daniel Thielen, Bill Anspach, and Jonathan Brauer, American Laboratory, Aug. 1999, pp. 13-21.
Article—*The Colloid Chemistry of Silica*, American Chemical Society 200th National Meeting, Aug. 26-31, 1990, pp. 22-23 and pp. 52-59.
Article—*Structure and properties of silica nanoclusters at high temperatures*, I. V. Schweigert, K. E. J. Lehtinen, M. J. Carrier, and M. R. Zachariah, The American Physical Society, Physical Review B, vol. 65, No. 235410, pp. 1-9.
Article—*Grafting of Poly(ethylenimine) onto Mesylated Cellulose Acetate, Poly(methyl methacrylate) and Poly(vinyl chloride)*, Christopher J. Biermann and Ramani Narayan, Carbohydrate Polymers, vol. 12, 1990, pp. 323-327.
Abstract of Article—*Non-hydrothermal synthesis of copper-, zinc-, and copper-zinc hydrosilicates*, T. M. Yurieva, G. N. Kustova, T. P. Minyukova, E. K. Poels, A. Bliek, M. P. Demeshkina, L. M. Plyasova, T. A. Krieger, and V. I. Zaikovskii, Materials Research Innovations, vol. 5, No. 1, Jun. 2001, pp. 3-11.
Pocket Guide to Digital Printing, Frank Cost, Delmar Publishers, Albany, NY ISBN 0-8273-7592-1, pp. 144-145.
Product Information Sheet for Snowtex®, 6 pages.
Abstract of Japanese Patent No. JP2002515826, May 28, 2002.
Article—*From Cyclodextrin Assemblies to Porous Materials by Silica Templating*, Polarz et al., Angew. Chem. Int. Ed. 2001, vol. 40, No. 23, pp. 4417-4421, 2001.

* cited by examiner

FIG. 1

ODOR CONTROL COMPOSITION

BACKGROUND OF THE INVENTION

Odor control additives have been conventionally incorporated into fibrous materials for a variety of reasons. For instance, U.S. Pat. No. 6,225,524 to Guarracino, et al. describes a substrate having an odor control composition that includes an absorbent gelling material and silica. Likewise, U.S. Pat. No. 6,376,741 to Guarracino, et al. describes a substrate having an odor control composition that includes silica and a zeolite (i.e., crystalline aluminosilicate). Unfortunately, conventional odor control compositions have proven to be ineffective in obtaining the full level of odor control desired when used in conjunction with absorbent articles.

As such, a need exists for an odor control composition that can exhibit improved odor control properties when applied to a substrate.

SUMMARY OF THE INVENTION

In accordance with one embodiment of the present invention, an odor control composition comprising a silicon oxide compound (e.g., silica, metal silicate, and so forth) formed from a silicon source and a cyclodextrin template is disclosed. The silicon source may be selected from the group consisting of alkoxy silanes (e.g., tetraethoxy silanes, tetrapropoxy silanes, tetrabutoxy silanes, etc.), silicone halides (e.g., silicone tetrafluoride, silicon tetrachloride, silicon tetrabromide, etc.), and combinations thereof. The cyclodextrin may be selected from the group consisting of $\alpha$-cyclodextrin, $\beta$-cyclodextrin, $\gamma$-cyclodextrin, $\delta$-cyclodextrin, derivatives thereof (e.g., hydroxyalkyl $\alpha$-cyclodextrin, alkyl $\alpha$-cyclodextrin, hydroxyalkyl $\beta$-cyclodextrin, alkyl $\beta$-cyclodextrin, hydroxyalkyl $\gamma$-cyclodextrin, alkyl $\gamma$-cyclodextrin, etc.), and combinations thereof. In some embodiments, the silicon oxide compound has a B.E.T. surface area of from about 100 square meters per gram to about 1500 square meters per gram, and in some embodiments, from about 500 square meters per gram to about 1000 square meters per gram. Further, the silicon oxide compound can have a median pore diameter of less than about 20 nanometers, in some embodiments less than about 10 nanometers, and in some embodiments, less than about 5 nanometers.

The odor control composition further comprises a transition metal that constitutes from about 0.2 wt. % to about 10 wt. %, in some embodiments from about 0.5 wt. % to about 5 wt. %, and in some embodiments, from about 1 wt. % to about 3 wt. % of the odor control composition. The transition metal may be selected from the group consisting of scandium, titanium, vanadium, chromium, manganese, iron, cobalt, nickel, copper, zinc, silver, and combinations thereof, and may or may not form part of the lattice of the silicon oxide compound.

In accordance with another embodiment of the present invention, an odor control composition is disclosed that comprises a silicon oxide compound formed from a silicon source and a template. The odor control composition further comprises a transition metal that constitutes from about 0.2 wt. % to about 10 wt. % of the odor control composition, wherein the silicon oxide compound has a median pore diameter of less than about 20 nanometers.

In accordance with still another embodiment of the present invention, a substrate is disclosed that is applied with an odor control composition. The odor control composition may constitute from about 0.5 wt. % to about 25 wt. %, and in some embodiments, from about 1 wt. % to about 10 wt. % of the substrate. The odor control composition comprises a silicon oxide compound and a transition metal in an amount of from about 0.2 wt. % to about 10 wt. % of the odor control composition.

In accordance with yet another embodiment of the present invention, a personal care absorbent article is disclosed that comprises at least one liquid-transmissive layer and a liquid-absorbent core. A substrate forms at least a portion of the liquid-transmissive layer, the liquid-absorbent core, or combinations thereof, wherein the substrate is applied with an odor control composition. The odor control composition comprises a silicon oxide compound and a transition metal in an amount of from about 0.2 wt. % to about 10 wt. % of the odor control composition.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Repeat use of reference characters in the present specification and drawings is intended to represent the same or analogous features or elements of the invention.

DETAILED DESCRIPTION OF REPRESENTATIVE EMBODIMENTS

Definitions

As used herein, an "absorbent article" refers to any article capable of absorbing water or other fluids. Examples of some absorbent articles include, but are not limited to, personal care absorbent articles, such as diapers, training pants, absorbent underpants, adult incontinence products, feminine hygiene products (e.g., sanitary napkins), swim wear, baby wipes, and so forth; medical absorbent articles, such as garments, fenestration materials, underpads, bandages, absorbent drapes, and medical wipes; food service wipers; clothing articles; and so forth. Materials and processes suitable for forming such absorbent articles are well known to those skilled in the art.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, bonded carded web processes, etc.

As used herein, the term "meltblowing" refers to a process in which fibers are formed by extruding a molten thermoplastic material through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that may be continuous or discontinuous, are generally smaller than 10 microns in diameter, and are generally tacky when deposited onto a collecting surface.

As used herein, the term "spunbonding" refers to a process in which small diameter substantially continuous fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spun-bonded nonwoven webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are incorporated herein in their entirety by reference thereto for all purposes. Spunbond fibers are generally not tacky when they are deposited onto a collecting surface. Spunbond fibers can sometimes have diameters less than about 40 microns, and are often between about 5 to about 20 microns.

DETAILED DESCRIPTION

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

In general, the present invention is directed to an odor control composition that contains a silicon oxide compound, such as silica, a metal silicate, etc. Silicon oxides exist with varying degrees of crystallinity, from fully crystalline to amorphous (non-crystalline), and can be derived from both natural sources (e.g., diatomaceous earth) and synthetic sources. For instance, in one particular embodiment, silica may be formed from a silicon source and a template. The silicon source may include, for example, alkoxy silanes, silicone halides (e.g., silicone tetrafluoride, silicon tetrachloride, silicon tetrabromide, etc.), and so forth. Some suitable alkoxy silane compounds that can be used in the present invention include, but are not limited to, tetraalkoxysilanes, such as tetramethoxy, tetraethoxy, tetrapropoxy and tetrabutoxy silanes. Particular examples of such silanes are tetramethylorthosilane (TMOS) or tetraethylorthosilane (TEOS).

A variety of templates may also be used to synthesize the microporous silica. Common examples of such templates include, but are not limited to, nonionic, cationic, anionic, and/or amphiphilic surfactants. For instance, ethylene oxide-based nonionic surfactants may be used as the template for silica synthesis. In another embodiment, cyclodextrins may be used as the template for silica synthesis. Some examples of cyclodextrins suitable for use in the present invention include, but are not limited to, α-cyclodextrin, β-cyclodextrin, γ-cyclodextrin, δ-cyclodextrin, composed of 6, 7, 8 and 9 D-glucose molecules, respectively. Derivatives of the aforementioned cyclodextrin molecules may also be used in the present invention, such as hydroxyalkyl α-cyclodextrin, alkyl α-cyclodextrin, hydroxyalkyl β-cyclodextrin, alkyl β-cyclodextrin, hydroxyalkyl γ-cyclodextrin, alkyl γ-cyclodextrin, and so forth. Silica prepared with a cyclodextrin template can have a variety of benefits. For example, cyclodextrins are ring-shaped polysaccharides that contain several molecules of D-glucose and are characterized by a cylindrical central hollow channel that serves as a receptacle for various molecules. The inner portions of this channel are generally hydrophobic, while the outer portions of the channel are generally hydrophilic. Thus, when placed in an aqueous solution, the cyclodextrin molecules become stacked in a long, channel-like arrangement. Accordingly, when the cyclodextrin-based solution is combined with a silicon source, the cyclodextrin molecules can define the pores in the resulting silica structure, corresponding to their long, channel-like shape. In this manner, the cyclodextrin acts as a "nanocasting" material for the silica and allows the pore size thereof to be readily controlled by simply varying the cyclodextrin molecule.

On a molar basis, the amount of the silicon source in the reaction mixture may be at least equal to and desirably several times greater than the amount of template. In particular, the molar ratio of template to the silicon source is generally in the range of from about $10^{-6}$ to about 1, and in some embodiments, from about $10^{-4}$ to about 1. The amount of water added to the mixture of the silicon source and template to effect hydrolysis of the silane compound is typically in the range of from about 1 to about 100 moles, and in some embodiments, from about 2 to about 30 moles per mole of the alkoxy silane compound.

The hydrolysis of the silicon source and gelation of the mixture is typically performed at a temperature in the range from about 20° C. to about 150° C., and in some embodiments, from about 40° C. to about 80° C. In some embodiments, the hydrolysis and silanol condensation of the silicon source may be accelerated by adding an acid or base to the mixture as a catalyst. Examples of suitable acid catalysts include, for instance, hydrochloric acid or acetic acid. In fact, when a small portion of the alkoxy silane compound is replaced with a silicon tetrahalide, e.g., silicon tetrachloride, as mentioned above, hydrolysis of the silicon tetrachloride can produce hydrogen chloride, which may serve as a catalyst to promote hydrolysis and gelation of the alkoxy silane compound.

Upon sufficient hydrolysis and gelation, the silica gel is then dried to remove any liquid components, e.g., water or methanol. The temperature at which the silica gel is dried or dehydrated normally does not exceed the decomposition temperature of the template. For example, the silica gel can be dried in a rotary evaporator under reduced pressure at a temperature of about 50° C. to about 100° C. into a dry form of the gel. The dried silica gel is then calcined to obtain a silica powder. Calcining may be carried out, for instance, under an oxygen-containing atmosphere at a temperature that does not cause the pore structure to substantially collapse, such as at a temperature of from about 300° C. to about 750° C., and in some embodiments, from about 400° C. to about 600° C. Upon calcination, the template is removed from the silica, leaving pores that can be used to adsorb various malodorous compounds.

In some embodiments, the silicon oxide compound can have a controlled, microporous pore size distribution, e.g., a median pore diameter of less than about 20 nanometers, in some embodiments less than about 10 nanometers, and in some embodiments, less than about 5 nanometers. The silicon oxide compound also typically has a relatively high surface area. For example, the silicon oxide compound may have a B.E.T. surface area of from about 100 $m^2/g$ to 1500 $m^2/g$, in some embodiments from 400 $m^2/g$ to about 1200 $m^2/g$, and in some embodiments, from about 500 $m^2/g$ to about 1000 $m^2/g$.

Without intending to be limited by theory, it is believed that such a small pore size distribution and high surface area can improve the adsorption capability of the silicon oxide compound for many malodorous compounds. Specifically, it is believed that a larger number of smaller pores may enable the silicon oxide compound to more selectively adsorb malodorous compounds than other compounds to which it is exposed.

In accordance with the present invention, the odor control composition also includes a transition metal. Examples of some suitable transition metals that can be used in the present invention include, but are not limited to, scandium, titanium, vanadium, chromium, manganese, iron, cobalt, nickel, copper, zinc, silver, and so forth. Without being limited by theory, it is believed that the presence of a transition metal in the odor control composition can improve the Lewis acidity of the silicon oxide compound and thus render it more receptive to free electron pairs of many malodorous compounds.

The transition metal may be incorporated into the odor control composition in a variety of ways. For instance, a transition metal salt and/or oxide may be combined with the silicon oxide compound before, during, and/or after its formation. For instance, some transition metal salts that may be used in the present invention include, but are not limited to, halides, such as iron chloride, copper chloride, etc.; sulfates; nitrates; acetates; oxalates; carbonates; and so forth. In some embodiments, the transition metal salt and/or oxide may be combined with the silicon oxide precursor materials, such as the silicon source and/or the template. When combined in this manner, it is believed that the transition metal of the salt and/or oxide may form part of the lattice of the silicon oxide compound by exchange of the metal with the silicon atoms, thereby forming a transition metal silicate. Of course, the transition metal salt may also be combined with the silicon oxide compound after it is synthesized. In such instances, it is believed that the transition metal is not typically incorporated into the lattice of the compound such that the resulting silicon oxide compound contains approximately 100 wt. % silica.

The relative amount of the transition metal in the odor control composition may vary depending on the nature of the transition metal, the substrate, the target malodorous compounds, and other factors. For instance, the presence of the transition metal is believed to improve odor adsorption of the silicon oxide compound at a relatively low concentration, but is also believed to actually reduce odor adsorption when used at too high of a concentration. Thus, in some embodiments, the transition metal may constitute from about 0.2 wt. % to about 10 wt. %, in some embodiments from about 0.5 wt. % to about 5 wt. %, and in some embodiments, from about 1 wt. % to about 3 wt. % of the odor control composition. Likewise, silicon oxide may constitute from about 90 wt. % to about 99.8 wt. %, in some embodiments from about 95 wt. % to about 99.5 wt. %, and in some embodiments, from about 97 wt. % to about 99 wt. % of the odor control composition.

In accordance with the present invention, the odor control composition described above is applied to a substrate to help reduce the production of odor in the environment to which the substrate is exposed. The amount of the composition may vary depending on the nature of the substrate and the intended application. However, in most embodiments, the odor control composition constitutes from about 0.5 to about 25 wt. % of the substrate, in some embodiments from about 1 to about 10 wt. % of the substrate, and in some embodiments, from about 2 to about 8 wt. % of the substrate. The odor control composition may be applied to a substrate using any of a variety of well-known application techniques. For instance, the composition may be incorporated within the matrix of the substrate and/or applied to the surface thereof. Suitable techniques for applying the composition to a substrate include printing, spraying, melt extruding, solvent coating, and so forth. In one particular embodiment, the odor control composition is dispersed within the fibers during formation of the substrate.

Any of a variety of different substrates may be incorporated with the odor control composition in accordance with the present invention. For instance, films, nonwoven fabrics, woven fabrics, knit fabrics, wet-strength paper, etc., may be applied with the odor control composition. When utilized, nonwoven fabrics may include, but are not limited to, spunbonded webs (apertured or non-apertured), meltblown webs, bonded carded webs, air-laid webs, coform webs, hydraulically entangled webs, and so forth.

In many cases, the substrate will form all or a portion of an absorbent article. Absorbent articles commonly include a liquid-transmissive bodyside liner, a liquid-transmissive surge layer below the bodyside liner, a liquid-absorbent core below the surge layer, and a moisture vapor permeable, liquid impermeable outer cover below the absorbent core. In some embodiments, the treated substrate of the present invention may be employed as any one or more of the liquid transmissive (non-retentive) and absorbent layers. An absorbent core of the absorbent article, for instance, may be formed from an absorbent nonwoven web that includes a matrix of hydrophilic fibers. In one embodiment, the absorbent web may contain a matrix of cellulosic fluff fibers. One type of fluff that may be used in the present invention is identified with the trade designation CR1654, available from U.S. Alliance, Childersburg, Ala., U.S.A., and is a bleached, highly absorbent sulfate wood pulp containing primarily soft wood fibers. In another embodiment, the absorbent nonwoven web may contain a hydoentangled web. Hydroentangling processes and hydroentangled composite webs containing various combinations of different fibers are known in the art. A typical hydroentangling process utilizes high pressure jet streams of water to entangle fibers and/or filaments to form a highly entangled consolidated fibrous structure, e.g., a nonwoven fabric. Hydroentangled nonwoven fabrics of staple length fibers and continuous filaments are disclosed, for example, in U.S. Pat. No. 3,494,821 to Evans and U.S. Pat. No. 4,144,370 to Bouolton, which are incorporated herein in their entirety by reference thereto for all purposes. Hydroentangled composite nonwoven fabrics of a continuous filament nonwoven web and a pulp layer are disclosed, for example, in U.S. Pat. No. 5,284,703 to Everhart, et al. and U.S. Pat. No. 6,315,864 to Anderson, et al., which are incorporated herein in their entirety by reference thereto for all purposes.

Another type of suitable absorbent nonwoven web is a coform material, which is typically a blend of cellulose fibers and meltblown fibers. The term "coform" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and so forth. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein in their entirety by reference thereto for all purposes.

If desired, the absorbent nonwoven web may also contain a superabsorbent material. Superabsorbents have the ability to absorb a great amount of fluid in relation to their own weight. Typical superabsorbents used in sanitary napkins can absorb anywhere from about 5 to about 60 times their weight in blood. Superabsorbent materials are produced in a wide variety of forms including, but not limited to, particles, fibers and flakes. Superabsorbents having a high mechanical stability in the swollen state, an ability to rapidly absorb fluid, and those having a strong liquid binding capacity, typically perform well in absorbent articles. Hydroxyfunctional polymers have been found to be good superabsorbents for this application. For example, a hydrogel-forming polymer, such as a partially neutralized cross-linked copolymer of polyacrylic acid and polyvinyl alcohol, can be utilized. After the polymer is formed, it is mixed with about a 1% anhydrous citric acid powder. The citric acid has been found to increase the ability of the superabsorbent to absorb menses and blood. This is particularly beneficial for use in a sanitary napkin or other feminine pads. The finely ground, anhydrous citric acid powder, which is void of water, along with trace amounts of fumed silica, is mixed with the polymer that may have been screened to an appropriate particle size. This mixture may also be formed into a composite or a laminate structure. Such superabsorbents can be obtained from Dow Chemical and Stockhausen, Inc., among others. This superabsorbent is a partially neutralized salt of cross-linked copolymer of polyacrylic acid and polyvinyl alcohol having an absorbency under load value above about 25. Some suitable superabsorbents are described in U.S. Pat. No. 4,798,603 to Meyers, et al., U.S. Pat. No. 32,649 to Brandt, et al. and U.S. Pat. No. 4,467,012 to Pedersen, et al., U.S. Pat. Nos. 4,604,313 and 4,655,757 to McFarland, et al., U.S. Pat. No. 6,387,495 to Reeves, et al., as well as in published European Patent Application 0,339,461 to Kellenberger.

As indicated above, the odor control composition may also be applied to a liquid transmissive layer of the absorbent article, such as the bodyside liner or surge layer. Such liquid transmissive layers are typically intended to transmit liquid quickly, and thus generally do not retain or absorb significant quantities of aqueous liquid. Materials that transmit liquid in such a manner include, but are not limited to, thermoplastic spunbonded webs, meltblown webs, bonded carded webs, air laid webs, and so forth. A wide variety of thermoplastic materials may be used to construct these non-retentive nonwoven webs, including without limitation polyamides, polyesters, polyolefins, copolymers of ethylene and propylene, copolymers of ethylene or propylene with a $C_4$-$C_{20}$ alpha-olefin, terpolymers of ethylene with propylene and a $C_4$-$C_{20}$ alpha-olefin, ethylene vinyl acetate copolymers, propylene vinyl acetate copolymers, styrene-poly(ethylene-alpha-olefin) elastomers, polyurethanes, A-B block copolymers where A is formed of poly(vinyl arene) moieties such as polystyrene and B is an elastomeric midblock such as a conjugated diene or lower alkene, polyethers, polyether esters, polyacrylates, ethylene alkyl acrylates, polyisobutylene, poly-1-butene, copolymers of poly-1-butene including ethylene-1-butene copolymers, polybutadiene, isobutylene-isoprene copolymers, and combinations of any of the foregoing.

Although various embodiments of substrates and absorbent articles have been described above, it should be understood that other embodiments are also contemplated in the present invention. In fact, the combination of the odor control composition may be used in conjunction with a variety of different substrates to achieve the benefits of the present invention.

Thus, as a result of the present invention, a substrate having improved odor control properties may be formed. Specifically, the particular selection of the silicon oxide compound and transition metal is believed to have a synergistic effect on the ability of the composition to reduce odors. For instance, the odor control composition can reduce odors, such as sulfur compounds, such as dimethyl disulfide (DMDS); ammonia; amines, such as trimethylamine (TMA), triethylamine (TEA), etc.; aldehydes; ketones; carboxylic acids; chlorinated ethanes, such as trichloroethane; etc. The odor control composition can also serve other functions as well. For instance, in one embodiment, the odor control composition may be used to adsorb ethylene produced by fruits to inhibit spoiling.

The present invention may be better understood with reference to the following examples.

Test Method

Odor adsorption was determined in the Examples using a test known as "Headspace Gas Chromatography." Headspace gas chromatography testing was conducted on an Agilent Technologies 5890, Series II gas chromatograph with an Agilent Technology 7694 headspace sampler (Agilent Technologies, Waldbronn, Germany). Helium was used as the carrier gas (injection port pressure: 12.7 psig; headspace vial pressure: 15.8 psig; supply line pressure is at 60 psig). A DB-624 column was used for the trimethylamine (TMA) and dimethyl disulfide (DMDS) that had a length of 30 meters and an internal diameter of 0.25 millimeters. Such a column is available from J&W Scientific, Inc. of Folsom, Calif. A HAYESEP P 60/80 column was used for the ammonia that had a length of 8 feet and an internal diameter of 0.085 inches. Such a column is available from Alltech Associates, Inc. of Deerfield, Ill. The operating parameters used for the headspace gas chromatography are shown below in Table 1:

TABLE 1

Operating Parameters for the Headspace Gas Chromatography Device.
Headspace Parameters

| | | |
|---|---|---|
| Zone Temps, ° C. | Oven | 37 |
| | Loop | 42 |
| | TR. Line | 47 |
| Event Time, minutes | GC Cycle time | 10.0 |
| | Vial eq. Time | 10.0 |
| | Pressuriz. Time | 0.20 |
| | Loop fill time | 0.20 |
| | Loop eq. Time | 0.15 |
| | Inject time | 0.30 |
| Vial Parameters | First vial | 1 |
| | Last vial | 1 |
| | Shake | [off] |

The test procedure involved placing 0.005-0.006 gram of the sample in a 20-cubic centimeter headspace vial. Using a syringe, an aliquot of the malodorous agent (TMA, ammonia, or DMDS) was also placed in the vial. The vial was then sealed with a cap and a septum and placed in the headspace gas chromatography oven at 37° C. After ten minutes, a hollow needle was inserted through the septum and into the vial. A 1-cubic centimeter sample of the headspace (air inside the vial) was then injected into the gas chromatograph.

Initially a control vial with only the aliquot of odoriferous agent (TMA, ammonia, or DMDS) was tested to define 0% odoriferous agent adsorption. To calculate the amount of headspace odoriferous agent removed by the sample, the peak area for the odoriferous agent from the vial with the sample was compared to the peak area from the odoriferous agent control vial. Testing was done with 3.8 milligrams of DMDS (3.6 microliters), 1.5 milligrams of $NH_3$ (6 microliters of a 28% $NH_3/H_2O$ solution), 2.0 milligrams of TMA (5.0 microliters of a 40% $TMA/H_2O$ solution), and 0.005-0.006 gram of the sample. Each sample was tested in duplicate.

EXAMPLE 1

The effectiveness of the odor control composition to adsorb malodorous compounds was demonstrated. Initially, a sample (Sample A) of a controlled pore size silica precursor was formed as follows. 20.0 grams of hydroxypropyl β-cyclodextrin (obtained from Cerestar) was added to 30.0 grams of distilled water in a 250 mL beaker that contained 0.643 gram of dissolved iron sulfate heptahydrate (obtained from Aldrich). Hydrochloric acid (37% HCl) was added to lower the pH of the solution to about 2. Then, 40.0 grams of tetramethyl orthosilicate (TMOS, 98%, Aldrich) was added and the solution was stirred for about 5 minutes before being transferred to a 500 mL round bottom flask. The flask was attached to a rot-a-vap for 10 minutes under vacuum at 40° C. to remove volatiles. The glass-like reaction product was chipped free of the flask the next day and then dried in a porcelain crucible for 17 hours at 110° C. To remove the cyclodextrin template, the sample was calcined using a procedure referred to as "excess oxygen", which involved placing the solid in a crucible with the lid slightly ajar and carrying out the calcination procedure in a muffle furnace in air for 17 hours at 460° C. The resulting iron-modified silica of Sample A had a Fe/Si mol ratio of 0.009, corresponding to 1.8 wt % Fe to Si.

Sample A was then tested for odor adsorption as described above. For comparative purposes, a control sample was also tested that was formed as described above, without the addition of a metal (Control #1). Further, various commercially available silica compositions were also tested. Control #2 was ZS™ 1115 MP, a precipitated silica obtained from Rhodia, Inc. of Cranbury, N.J.; Control #3 was Tixosil™ 38A, a precipitated silica obtained from Rhodia, Inc. of Cranbury, N.J.; and Control #4 was Britesorb™ C930, a food-grade silica gel obtained from PQ Corp. of Valley Forge, Pa.

The results are shown below in Table 2 in terms of milligrams of the malodorous compound removed per gram of sample.

TABLE 2

| | Odor Adsorption Characteristics | | |
|---|---|---|---|
| Sample | mg of $NH_3$ removed/g of sample | mg of TMA removed/g of sample | mg of DMDS removed/g of sample |
| A | 64 ± 11 | 88 ± 9 | 221 ± 5 |
| Control #1 | 42 ± 1 | 63 ± 8 | 187 ± 5 |
| Control #2 | 28 ± 3 | 29 ± 5 | 44 ± 4 |
| Control #3 | 53 ± 15 | 44 ± 2 | 69 ± 3 |
| Control #4 | 41 ± 1 | 41 ± 1 | 81 ± 4 |

As indicated, Sample A had a higher adsorption of DMDS, TMA, and $NH_3$ than the control samples.

EXAMPLE 2

A sample (Sample B) of a controlled pore size silica precursor was formed as described in Example 1, except that a calcining procedure referred to as "limited oxygen" was utilized. This calcining procedure involved placing the solid in a crucible with a tight fitting lid and calcining in a muffle furnace in air for 17 hours at 460° C. The resulting iron-modified silica of Sample B had a Fe/Si mol ratio of 0.009, corresponding to 1.8 wt % Fe to Si.

The surface area was determined by the physical gas adsorption (B.E.T.) method of Bruanauer, Emmet, and Teller, Journal of American Chemical Society, Vol 60, 1938, p. 309, with nitrogen as the adsorption gas. The analysis was performed by Micromeritics Instrument Corp. of Norcross, Georgia using an ASAP 2010 Physical Adsorption Analyzer. The B.E.T. surface area was determined to be 733 $m^2/g$. The median pore diameter was also determined to be 1.9 nanometers from the isotherm data.

Figure 1:
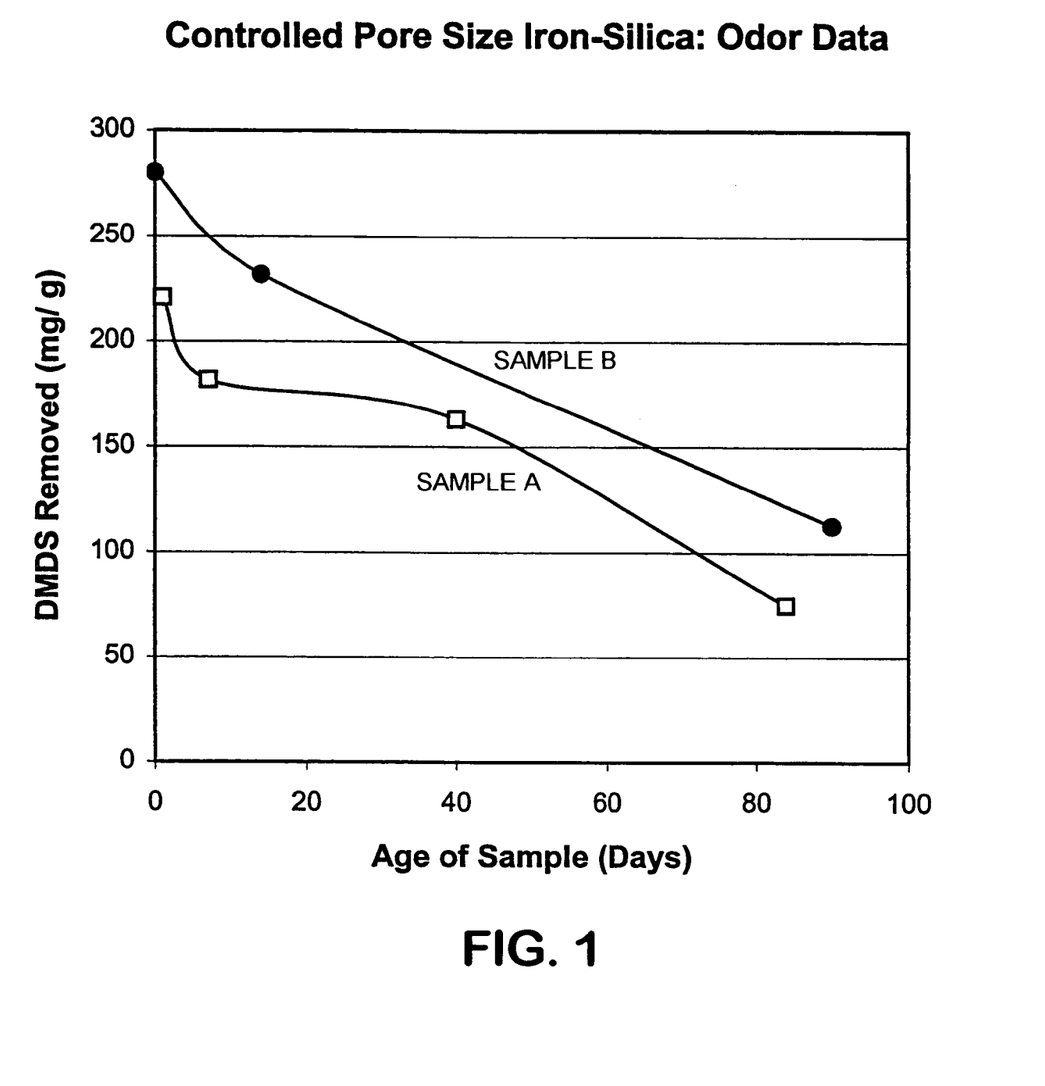
FIG. 1 shows the amount of DMDS removed versus the days aged in Example 2.

In addition, Sample A (Example 1) and Sample B (Example 2) were both aged for about 90 days at room temperature and a relative humidity of 50%. The odor adsorption of DMDS was tested for the aged samples as described above. The results are shown in FIG. 1. As indicated, the sample formed with "limited air" calcination (Sample B) appeared to have a better odor adsorption of DMDS upon aging than the sample formed with "excess air" calcination (Sample A).

EXAMPLE 3

The effectiveness of the odor control composition to adsorb malodorous compounds was demonstrated. Initially, a sample (Sample C) of a controlled pore size silica precursor was formed as follows. 20.0 grams of hydroxypropyl β-cyclodextrin (obtained from Cerestar) was added to 30.0 grams of distilled water in a 250 mL beaker that contained 0.300 gram of dissolved copper chloride (obtained from Aldrich). Hydrochloric acid (37% HCl) was added to lower the pH of the solution to about 2. Then, 40.0 grams of tetramethyl orthosilicate (TMOS, 98%, Aldrich) was added and the solution was stirred for about 5 minutes before being transferred to a 500 mL round bottom flask. The flask was attached to a rot-a-vap for 10 minutes under vacuum at 40° C. to remove volatiles. The glass-like reaction product was chipped free of the flask the next day and then dried in a porcelain crucible for 17 hours at 110° C. Sample C was calcined using the "excess oxygen" procedure referred to in Example 1. The resulting copper-modified silica of Sample C had a Cu/Si mol ratio of 0.008, corresponding to 1.9 wt % Cu to Si.

Sample C was then tested for odor adsorption as described above and compared to the control samples of Example 1. The results are shown below in Table 3 in terms of milligrams of the malodorous compound removed per gram of sample.

TABLE 3

| | Odor Adsorption Characteristics | | |
|---|---|---|---|
| Sample | mg of $NH_3$ removed/g of sample | mg of TMA removed/g of sample | mg of DMDS removed/g of sample |
| C | 66 ± 1 | 84 ± 3 | 191 ± 0 |
| Control #1 | 42 ± 1 | 63 ± 8 | 187 ± 5 |
| Control #2 | 28 ± 3 | 29 ± 5 | 44 ± 4 |
| Control #3 | 53 ± 15 | 44 ± 2 | 69 ± 3 |
| Control #4 | 41 ± 1 | 41 ± 1 | 81 ± 4 |

As indicated, Sample C had a much higher adsorption of TMA and $NH_3$ than the control samples. In addition, the DMDS adsorption of Sample C was also much higher than Controls #2, #3, and #4.

In another test, Sample C and Control #1 (Example 1) were aged for about 5½ months at room temperature and a relative humidity of 50%. Thereafter, the aged samples were dried in air for 10 hours at 135° C. The odor adsorption of DMDS was tested for the aged samples as described above. The results are shown below in Table 4.

TABLE 4

Aged Odor Adsorption Characteristics for DMDS

| Sample | mg of DMDS removed/g of sample (Initial)* | mg of DMDS removed/g of sample (Aged) | mg of DMDS removed/g of sample (Aged and Dried) |
| --- | --- | --- | --- |
| C | 191 | 84 | 108 |
| Control #1 | 187 | 103 | 137 |

*Collected within about 1 day of sample preparation

As indicated above, Sample C maintained a good relative adsorption efficiency after aging and drying. Although Sample C had a lower relative adsorption efficiency than Control #1 after aging, it should be understood that the pore structure and surface chemistry of any given odor control composition or substrate may not be suitable to reduce all types of odors, and that low adsorption of one or more malodorous compounds, before or after aging, may be compensated by good adsorption of other malodorous compounds. In addition, as shown above, the reduction in adsorption efficiency upon aging is reversed after drying. Without intending to be limited in theory, it is believed that water molecules present within the aged composition may somewhat reduce odor adsorption, particularly for odors such as DMDS that are not soluble in water. Thus, odor adsorption can be further improved by drying to remove such excess water molecules.

EXAMPLE 4

A sample (Sample D) of a controlled pore size silica precursor was formed as described in Example 3, except that the "limited oxygen" calcining procedure referred to in Example 2 was utilized. The resulting copper-modified silica of Sample D had a Cu/Si mol ratio of 0.008, corresponding to 1.9 wt % Cu to Si.

Sample C (Example 3), Sample D (Example 4), and Control #1 (Example 1) were aged for about 5 months at room temperature and a relative humidity of 50%. Thereafter, the aged samples were dried in air for 13 hours at 115° C. The odor adsorption of DMDS was tested for the aged samples as described above. The results are shown below in Table 5.

TABLE 5

Aged Odor Adsorption Characteristics for DMDS

| Sample | mg of DMDS removed/g of sample (Initial)* | mg of DMDS removed/g of sample (Aged) | mg of DMDS removed/g of sample (Aged and Dried) |
| --- | --- | --- | --- |
| C | 191 | 77 | 90 |
| D | 222 | 104 | 157 |
| Control #1 | 187 | 69 | Not tested |

*Collected within about 1 day of sample preparation

As indicated, the sample formed with "limited air" calcination appeared to have a better odor adsorption of DMDS upon aging than the sample formed with "excess air" calcination. It can also be seen that drying improves the DMDS odor adsorption of the sample calcined under "limited air" to a greater extent than that calcined under "excess air."

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A substrate that contains an odor control composition in an amount of from about 0.5 wt. % to about 25 wt. % of the substrate, wherein said odor control composition comprises a silicon oxide compound and a transition metal that constitutes from about 0.2 wt. % to about 10 wt. % of said odor control composition, wherein said silicon oxide compound is formed from a silicon source and a cyclodextrin template.

2. A substrate as defined in claim 1, wherein said silicon source is selected from the group consisting of alkoxy silanes, silicone halides, and combinations thereof.

3. A substrate as defined in claim 1, wherein said silicon source is selected from the group consisting of tetraethoxy silanes, tetrapropoxy silanes, tetrabutoxy silanes, and combinations thereof.

4. A substrate as defined in claim 1, wherein said cyclodextrin is selected from the group consisting of α-cyclodextrin, β-cyclodextrin, γ-cyclodextrin, δ-cyclodextrin, derivatives thereof, and combinations thereof.

5. A substrate as defined in claim 1, wherein said transition metal is selected from the group consisting of scandium, titanium, vanadium, chromium, manganese, iron, cobalt, nickel, copper, zinc, silver, and combinations thereof.

6. A substrate as defined in claim 1, wherein said silicon oxide compound has a B.E.T. surface area of from about 100 square meters per gram to about 1500 square meters per gram.

7. A substrate as defined in claim 1, wherein said silicon oxide compound has a B.E.T. surface area of from about 500 square meters per gram to about 1000 square meters per gram.

8. A substrate as defined in claim 1, wherein said silicon oxide compound has a median pore diameter of less than about 20 nanometers.

9. A substrate as defined in claim 1, wherein said silicon oxide compound has a median pore diameter of less than about 10 nanometers.

10. A substrate as defined in claim 1, wherein said transition metal constitutes from about 0.5 wt. % to about 5 wt. % of said odor control composition.

11. A substrate as defined in claim 1, wherein said odor control composition constitutes from about 0.5 wt. % to about 25 wt. % of the substrate.

12. A substrate as defined in claim 1, wherein said odor control composition constitutes from about 1 wt. % to about 10 wt. % of the substrate.

13. A substrate as defined in claim 1, wherein said silicon oxide compound is a metal silicate, said transition metal forming at least a portion of said metal silicate.

14. A substrate as defined in claim 1, wherein said silicon oxide compound includes approximately 100 wt. % silica.

15. A substrate as defined in claim 1, wherein said silicon oxide compound has a B.E.T. surface area of from about 400 square meters per gram to about 1200 square meters per gram.

16. A substrate as defined in claim 1, wherein said silicone oxide constitutes from about 90 wt. % to about 99.8 wt. % of said odor control composition.

17. A substrate as defined in claim 1, wherein said substrate is selected from the group consisting of films, nonwoven fabrics, woven fabrics, knit fabrics, paper and combinations thereof.

18. A substrate as defined in claim 17, wherein said substrate is an absorbent web containing cellulosic fibers.

19. A substrate as defined in claim 17, wherein said substrate is a nonwoven web selected from the group consisting of spunbonded webs, meltblown webs, bonded carded webs, airlaid webs, and combinations thereof.

20. A nonwoven web that contains an odor control composition in an amount of from about 0.5 wt. % to about 25 wt. % of the nonwoven web, wherein said odor control composition comprises a silicon oxide compound and a transition metal that constitutes from about 0.2 wt. % to about 10 wt. % of said odor control composition, wherein said silicon oxide compound is formed from a silicon source and a template, wherein said silicon oxide compound has a median pore diameter of less than about 20 nanometers.

21. A nonwoven web as defined in claim 20, wherein said silicon oxide compound is a metal silicate, said transition metal forming at least a portion of said metal silicate.

22. A nonwoven web as defined in claim 20, wherein said silicon oxide compound includes approximately 100 wt. % silica.

23. A nonwoven web as defined in claim 20, wherein said silicon source is selected from the group consisting of alkoxy silanes, silicone halides, and combinations thereof.

24. A nonwoven web as defined in claim 20, wherein said silicon source is selected from the group consisting of tetraethoxy silanes, tetrapropoxy silanes, tetrabutoxy silanes, and combinations thereof.

25. A nonwoven web as defined in claim 20, wherein said template is a cyclodextrin selected from the group consisting of α-cyclodextrin, β-cyclodextrin, γ-cyclodextrin, δ-cyclodextrin, derivatives thereof, and combinations thereof.

26. A nonwoven web as defined in claim 20, wherein said transition metal is selected from the group consisting of scandium, titanium, vanadium, chromium, manganese, iron, cobalt, nickel, copper, zinc, silver, and combinations thereof.

27. A nonwoven web as defined in claim 20, wherein said silicon oxide compound has a B.E.T. surface area of from about 100 square meters per gram to about 1500 square meters per gram.

28. A nonwoven web as defined in claim 20, wherein said silicon oxide compound has a B.E.T. surface area of from about 400 square meters per gram to about 1200 square meters per gram.

29. A nonwoven web as defined in claim 20, wherein said silicon oxide compound has a B.E.T. surface area of from about 500 square meters per gram to about 1000 square meters per gram.

30. A nonwoven web as defined in claim 20, wherein said silicon oxide compound has a median pore diameter of less than about 10 nanometers.

31. A nonwoven web as defined in claim 20, wherein said transition metal constitutes from about 0.5 wt. % to about 5 wt. % of said odor control composition.

32. A nonwoven web as defined in claim 20, wherein said odor control composition constitutes from about 0.5 wt. % to about 25 wt. % of said nonwoven web.

33. A nonwoven web as defined in claim 20, wherein said odor control composition constitutes from about 1 wt. % to about 10 wt. % of said nonwoven web.

34. A nonwoven web as defined in claim 20, wherein said silicone oxide constitutes from about 90 wt. % to about 99.8 wt. % of said odor control composition.

35. A nonwoven web as defined in claim 20, wherein said nonwoven web is a spunbonded web, a meltblown web, or a combination thereof.

36. A nonwoven web as defined in claim 20, wherein said nonwoven web is an absorbent nonwoven web containing cellulosic fibers.

* * * * *

UNITED STATES PATENT AND TRADEMARK OFFICE
CERTIFICATE OF CORRECTION

| | |
|---|---|
| PATENT NO. | : 7,582,308 B2 |
| APPLICATION NO. | : 10/328730 |
| DATED | : September 1, 2009 |
| INVENTOR(S) | : Quincy, III et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1169 days.

Signed and Sealed this

Fourteenth Day of September, 2010

David J. Kappos
*Director of the United States Patent and Trademark Office*